United States Patent
Adami et al.

(10) Patent No.: US 7,323,593 B2
(45) Date of Patent: Jan. 29, 2008

(54) METHOD AND DEVICE FOR PRODUCING FORMATES AND THE USE THEREOF

(75) Inventors: Christoph Adami, Weinheim (DE); Jörn Karl, Mannheim (DE); Alexander Hauk, Ludwigshafen (DE); Ralf Böhling, Griesheim (DE); Jörg Pastre, Bensheim (DE); Robert Lenz, Hochdorf-Assenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 557 days.

(21) Appl. No.: 10/524,202

(22) PCT Filed: Jul. 30, 2003

(86) PCT No.: PCT/EP03/08400

§ 371 (c)(1),
(2), (4) Date: Feb. 10, 2005

(87) PCT Pub. No.: WO2004/022517

PCT Pub. Date: Mar. 18, 2004

(65) Prior Publication Data

US 2005/0256338 A1  Nov. 17, 2005

(30) Foreign Application Priority Data

Aug. 12, 2002 (DE) ............................... 102 37 380

(51) Int. Cl.
*C07C 53/00* (2006.01)
(52) U.S. Cl. ..................................................... 562/609
(58) Field of Classification Search ..................... None
See application file for complete search history.

(56) References Cited

U.S. PATENT DOCUMENTS

| | | | |
|---|---|---|---|
| 4,261,755 A | 4/1981 | Berry et al. | |
| 4,299,981 A | 11/1981 | Jackson | |
| 4,326,073 A | 4/1982 | Wolf et al. | |
| 5,935,625 A | 8/1999 | Ploenes et al. | |
| 6,906,222 B2 * | 6/2005 | Slany et al. | 562/609 |
| 2003/0092939 A1 | 5/2003 | Strofer et al. | |

FOREIGN PATENT DOCUMENTS

| | | |
|---|---|---|
| DE | 101 54 757 A1 | 5/2003 |
| DE | 102 10 730 A1 | 9/2003 |

(Continued)

OTHER PUBLICATIONS

Bilbiothek, Gmelins Handbuch der Anorganischen Chemie. Achte Vollig neu Bearbeitete Auflage. NATRIUM Mit 75 Figuren, System-Nummer 21. BERLIN (1928) pp. 816-819.

(Continued)

*Primary Examiner*—Karl Puttlitz
(74) *Attorney, Agent, or Firm*—Connolly Bove Lodge and Hutz

(57) ABSTRACT

A process for preparing acid formates which comprises
(a) partially hydrolyzing methyl formates with water;
(b) separating off by distillation methyl formate and methanol from the reaction mixture obtained in process stage (a), forming a stream comprising formic acid and water; and
(c) combining the stream comprising formic acid and water from the process stage (b) and the corresponding formate, forming a mixture comprising the acid formate and water,
an apparatus for their preparation and their use.

18 Claims, 2 Drawing Sheets

FOREIGN PATENT DOCUMENTS

| | | |
|---|---|---|
| EP | 0 005 998 A1 | 12/1979 |
| EP | 0 017 866 | 10/1980 |
| WO | WO-96/35657 | 11/1996 |
| WO | WO-98/20911 | 5/1998 |
| WO | WO-00/08929 | 2/2000 |

OTHER PUBLICATIONS

Haupibucherei, Gmelins Handbuch der anorganischen Chemie, 8, Auflage. Herausgegeben von der Deutschen Chemischen Gesellschaft. System-Nummer 22: Kalium. Lieferung 3 Verbindungen bis Kalium und Tellur. BERLIN (1937) pp. 919-921.

Deutches Reich Reichspatetamt Patentschrift. Firma Rudolph Koepp & Co. in Oestrich i. Rhg. und Dr. Egon Elod in Karlsruhe i.B. Patentiert im Deutschen Reiche vom 27. Juni 1923 ab.

The Journal of the American Chemical Society. Vol. XLIII Jul.-Dec. 1921 pp. 1470-1481. Compound Formation and Solubility in Systems of the Type, Formic Acid: Metal Formate (by James Kendall and Howard Adler Feb. 25, 1921).

Ullmann's Encyclopedia of Industrial Chemistry, Sixth Edition, 2000 Electronic Release Formic Acid—Production (Werner Reutemann, Heinz Kieczka).

* cited by examiner

METHOD AND DEVICE FOR PRODUCING FORMATES AND THE USE THEREOF

CROSS REFERENCE TO RELATED APPLICATION

The present application is a National Stage application of PCT/EP2003/008400, filed Jul. 30, 2003, which claims priority from German Patent Application No. DE 102 37 380.9, filed Aug. 12, 2002.

The present invention relates to a process and an apparatus for preparing acid formates starting from methyl formate, water and a basic compound.

In addition, the invention relates to the use of the acid formates for preserving and/or acidifying plant and/or animal materials, for treating biowastes and as an additive in animal nutrition and/or as growth promoters for animals.

Acid formates have an antimicrobial activity and are used, for example, for preserving and for acidifying plant and animal materials, for instance grasses, agricultural products or meat, for treating biowastes or as an additive for animal nutrition.

Acid formates and preparation methods for these have long been known. Thus, Gmelins Handbuch der anorganischen Chemie [Gmelin's Handbook of Inorganic Chemistry], 8th edition, Number 21, pages 816 to 819, Verlag Chemie GmbH, Berlin 1928 and Number 22, pages 919 to 921, Verlag Chemie GmbH, Berlin 1937 describes the synthesis of sodium diformate and of potassium diformate by dissolving sodium formate and potassium formate in formic acid. The crystalline diformates may be obtained by decreasing the temperature and by evaporating off excess formic acid.

DE 424 017 teaches preparing acid sodium formates having varying acid content by introducing sodium formate into aqueous formic acid in an appropriate molar ratio. By cooling the solution the corresponding crystals can be obtained.

According to J. Kendall et al., Journal of the American Chemical Society, Vol. 43, 1921, pages 1470 to 1481, acid potassium formates may be obtained by dissolving potassium carbonate in 90% strength formic acid, forming carbon dioxide. The corresponding solids can be obtained by crystallization.

U.S. Pat. No. 4,261,755 describes preparing acid formates by reacting an excess of formic acid with the hydroxide, carbonate or bicarbonate of the corresponding cation.

WO 96/35657 teaches preparing products which contain disalts of formic acid by mixing potassium formate, hydroxide, carbonate or bicarbonate, sodium formate, hydroxide, carbonate or bicarbonate, cesium formate, hydroxide, carbonate or bicarbonate or ammonium formate or ammonia with, possibly aqueous, formic acid, subsequently cooling the reaction mixture, filtering the resultant slurry and drying the resultant filter cake and recirculating the filtrate.

A disadvantage of the abovementioned processes is that, per mole of formate formed by the reaction with the basic compounds, in each case one mole of formic acid is consumed. This is because, as is known, it is precisely the preparation of concentrated, that is to say substantially anhydrous, formic acid, which is a process which requires extensive equipment, and is costly and energy-consuming. Thus the abovementioned processes, based on the entire value-added chain, require extensive equipment and are costly and energy-consuming.

German application No. 102 10 730.0 teaches preparing acid formates by reacting methyl formate with water and a basic compound having a $PK_a$ of the conjugate acid of the appropriate dissociation state of $\geq 3$, and subsequently removing the methanol formed and optionally setting the desired acid content by adding formic acid.

German application No. 101 54 757.9 teaches preparing metal formate/formic acid mixtures by carbonylating the corresponding metal hydroxide to give the metal formate in the presence of water and a catalyst, removing the water and the catalyst by distillation and adding formic acid to the metal formate to produce the desired metal formate/formic acid mixture.

It is an object of the present invention, therefore, to provide a process which no longer has the abovementioned disadvantages, which makes it possible to prepare acid formates on an industrial scale in high yield and high space-time yield, with simultaneously high flexibility with respect to composition and with the use of readily accessible raw materials and which permits a simple process procedure with low capital costs and low energy consumption.

We have found that this object is achieved by a process for preparing acid formates, which comprises (a) partially hydrolyzing methyl formates with water;

(b) separating off by distillation methyl formate and methanol from the reaction mixture obtained in process stage (a), forming a stream comprising formic acid and water; and (c) combining the stream comprising formic acid and water from the process stage (b) with the corresponding formate, forming a mixture comprising the acid formate and water.

Figure 1:
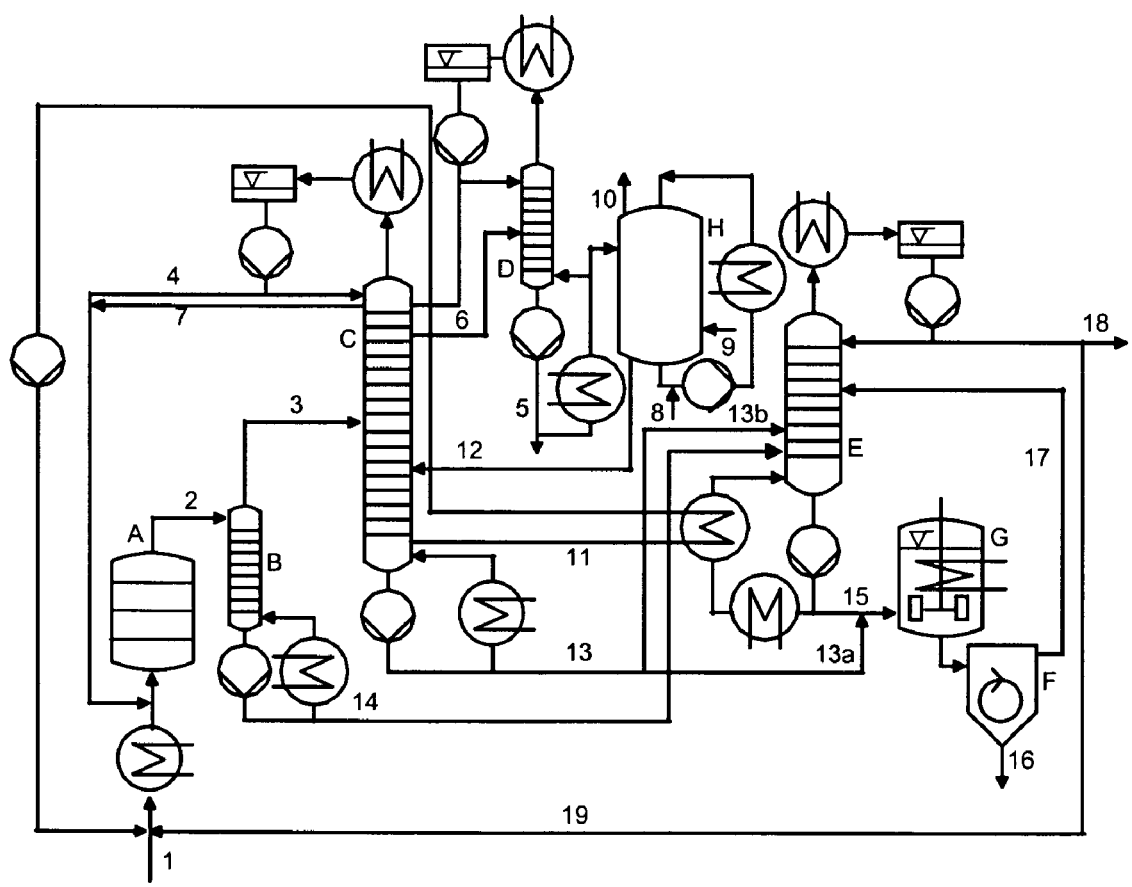
FIG. 1 is a process flow chart of the instant invention.

Acid formates are compounds and mixtures which contain formate anions ($HCOO^-$), cations ($M^{x+}$) and formic acid ($HCOOH$). They can occur together in the form of a solid or a liquid and if appropriate contain other components, for example other salts, additives or solvents such as water. Generally, the acid formates can be represented by the formula

$$HCOO^- M^{x+}_{1/x} \cdot y HCOOH \qquad (I),$$

where M is a monovalent or polyvalent inorganic or organic cation, x is a positive integer and indicates the charge of the cation and y gives the molar fraction of formic acid based on the formate anion. The molar fraction of formic acid based on the formate anion y is generally from 0.01 to 100, preferably from 0.05 to 20, particularly preferably from 0.5 to 5, and in particular from 0.9 to 3.1.

The nature of the inorganic or organic cation $M^{x+}$ is in principle not critical, provided that this is stable under conditions under which the acid formate is to be handled. This also includes, for example, stability toward the reducing formate anion. Possible inorganic cations are the monovalent and/or polyvalent metal cations of metals of groups 1 to 14 of the Periodic Table of the Elements, for example lithium ($Li^+$), sodium ($Na^+$), potassium ($K^+$), cesium ($Cs^+$), magnesium ($Mg^{2+}$), calcium ($Ca^{2+}$), strontium ($Sr^{2+}$) and barium ($Ba^{2+}$), preferably sodium ($Na^+$), potassium ($K^+$), cesium ($Cs^+$) and calcium ($Ca^{2+}$). Possible organic cations are unsubstituted ammonium ($NH_4^+$) and ammonium substituted by one or more carbon-containing radicals which may also be linked to one another, for example methylammonium, dimethylammonium, trimethylammonium, ethylammonium, diethylammonium, triethylammonium, pyrollidinium, N-methylpyrroldinium, piperidinium, N-methylpiperidinium or pyridinium.

A carbon-containing organic radical is an unsubstituted or substituted, aliphatic, aromatic or araliphatic radical having from 1 to 30 carbons. This radical can contain one or more heteroatoms, such as oxygen, nitrogen, sulfur or phosphorus, for example —O—, —S—, —NR—, —CO—, —N=, —PR— and/or —PR$_2$ and/or be substituted by one or more functional groups which, for example, contain oxygen, nitrogen, sulfur and/or halogen, for example by fluorine, chlorine, bromine, iodine and/or a cyano group (the radical R here is also a carbon-containing organic radical). The carbon-containing organic radical can be a monovalent or polyvalent radical, for example divalent or trivalent radical.

The individual process stages are described in more detail below:

Process Stage (a)

In process stage (a), methyl formate is partially hydrolyzed with water to formic acid and methanol. Partially means that only a portion of the methyl formate fed is hydrolyzed.

In the inventive process, in process stage (a) processes which are known per se for hydrolyzing methyl formate can be used. A general overview of known and industrially relevant processes for hydrolysis is given, for example, in Ullmann's Encyclopedia of Industrial Chemistry, 6$^{th}$ edition, 2000 electronic release, Chapter "FORMIC ACID, Production". Other suitable hydrolysis processes are also described, for example, in EP-A 0 005 998 and EP-A 0 017 866.

The hydrolysis is generally carried out at a temperature of from 80 to 150° C. and a pressure of from 0.5 to 2.0 MPa absolute. Reaction apparatuses which can be used are in principle all reaction apparatuses which are suitable for reactions in the liquid phase. Examples are stirred tanks and jet loop reactors. Preference is given to the use of a cascade reactor.

Generally, it is advantageous to carry out the hydrolysis in the presence of an acid catalyst, since this significantly increases the hydrolysis rate. Acid catalysts which can be used are the formic acid which is formed or additional catalysts. The additional catalysts can be of homogeneous or heterogeneous nature. Examples of heterogeneous catalysts are acid ion-exchangers, for example polysulfonic acids or poly(perfluoroalkylene)sulfonic acids (for example Nafion® from Du Pont) and examples of homogeneous catalysts are strong inorganic or organic acids, such as sulfuric acid, hydrochloric acid or alkyl- and tolylsulfonic acids. If homogeneous catalysts are used, these must generally be removed in a subsequent stage. Depending on the desired purity of the acid formates to be prepared, however, it is also possible to allow these to remain in the system. In this case, the acid catalysts are usually recovered in the form of their salts in the acid formate. Particularly preferably, the partial hydrolysis is carried out in the presence of formic acid as acid catalyst, which avoids adding an additional catalyst and its subsequent removal or possible contamination of the acid formates. Generally, for this purpose, at the reactor inlet a formic acid concentration of from about 0.1 to 2% by weight, based on the liquid mixture present which contains water and methyl formate, is established, by targeted addition of formic acid or a stream comprising formic acid.

The molar ratio of methyl formate to water to be used in the hydrolysis in the inventive process is generally from 0.1 to 10. Since this is an equilibrium reaction, an excess of water is preferably used, as also follows, for example, from the teaching of EP-A 0 017 866. Preferably in process stage (a), the methyl formate and the water are fed in a molar ratio of from 0.1 to 1, and particularly preferably from 0.15 to 0.3.

The reaction mixture obtained from the partial hydrolysis thus comprises unreacted methyl formate, formic acid, methanol and, owing to the preferred use of an excess of water, water. Preferably, the aqueous reaction mixture comprises from 5 to 15 mol %, particularly preferably from 8 to 12 mol %, formic acid, from 3 to 10 mol %, particularly preferably from 6 to 12 mol %, methyl formate and from 6 to 15 mol %, particularly preferably from 8 to 12 mol %, methanol.

Process Stage (b)

In process stage (b), methyl formate and methanol are removed by distillation from the reaction mixture obtained in process stage (a), forming a stream comprising formic acid and water. Methyl formate and methanol can here in principle be removed together in the form of a stream or separately in the form of a stream comprising methyl formate and a stream comprising methanol. Generally, methyl formate and methanol are taken off separately or together in the upper part of the column. The stream comprising formic acid and water is generally taken off from the bottom. Preference is given in process stage (b) to the joint removal of a stream comprising methyl formate and methanol.

The design and operation of the distillation column is primarily dependent on the composition of the stream which is fed and on the desired purities of the two product streams and can be determined in a known way by those skilled in the art.

The methyl formate separated off in process stage (b) is preferably recirculated to process stage (a). If, in process stage (b), as is preferred, methyl formate and methanol are separated off together in the form of a joint stream, preferably the methyl formate, before it is recirculated, is substantially freed from methanol by distillation. This is generally performed in a column downstream of the column of process stage (b). Since methyl formate is generally prepared by carbonylating methanol, it is particularly advantageous to recirculate the stream comprising the remaining methanol as starting material for the preparation of methyl formate, in which case the methanol to be recirculated in this variant can certainly still contain residual amounts of methyl formate. Thus it is only necessary in the overall balance to replace the small methanol losses by fresh methanol.

Process Stage (c)

In process stage (c), the stream from process stage (b) which comprises formic acid and water is combined with the corresponding formate, forming a mixture comprising the acid formate and water.

The formates to be used can generally be represented by the formula (II)

$$HCOO^-M^{x+}{}_{1/x} \qquad (II),$$

where M and x have the meaning specified under (I). Preferably, sodium formate, potassium formate and/or calcium formate is used in the inventive process, and particularly preferably sodium formate and/or potassium formate.

The manner in which the formates to be used are added is generally not critical in the inventive process. They can be added in solid or liquid form, as pure substance, as mixture of substances or as solution. Examples are addition in the form of aqueous solutions (for example aqueous solutions of the alkali metal formates) and addition in the form of solid compounds (for example powders of the alkali metal formates). Preference is given to addition in the form of aqueous solutions.

The order in which the stream from the process stage (b) which comprises formic acid and water and the corresponding formate are added is generally not critical in the inventive process. In particular, it is possible and may be advantageous, before they are combined, to concentrate formic acid in the stream from process stage (b) which comprises formic acid and water. In this context, mention may be made, in particular, of removing a portion of the water present by evaporation, preferably by distillation.

Temperature and pressure are generally not critical for the combining operation in process stage (c). Generally they are combined at a temperature of from 0 to 150° C. and a pressure of from 0.01 to 0.3 MPa absolute.

Apparatuses which can be used are in principle all apparatuses which are suitable for reactions in the liquid phase and, if appropriate, for reactions in the liquid phase with simultaneous removal of a volatile component. Examples are stirred tanks, jet loop reactors and columns. In addition, it is also possible, for example, to combine the two streams by their meeting within a pipe, advantageously having a downstream mixing section. In addition, it is also possible to combine the two streams in the apparatus in which solid acid formate is also isolated.

The mixture obtained by combining the stream comprising the formic acid and the water from the process stage (b) and the corresponding formate comprises the acid formate in the form of an aqueous solution, with or without previously precipitated acid formate as solid. Depending on requirements, it can in this form be packaged, stored, transported and/or used for appropriate formulations or uses. In addition, the acid formate can be further concentrated or isolated as solid by downstream process steps.

Preference is given to a variant in which, in the process stage (c)
(i) the stream comprising the formic acid and the water from process stage (b), together with the mother liquor recirculated from step (iv) is concentrated in a column or an evaporator with removal of water by distillation;
(ii) the stream which was produced from step (i) by concentration and which comprises formic acid, water and formate is combined with the corresponding formate forming a mixture comprising the acid formate and water;
(iii) solid acid formate from the mixture comprising acid formate and water which is obtained from step (ii) is precipitated by crystallization and this is isolated; and
(iv) The resultant mother liquor is recirculated to step (i).

The column or the evaporator in step (i) is generally to be operated in such a manner that a portion of the water fed can be taken off, for example overhead. The remaining stream comprising formic acid, water and formate generally has a water content of from 10 to 40% by weight and is withdrawn as bottoms product. Said procedure has the advantage of a certain concentration of the stream comprising the formic acid and the formate. The water withdrawn from the column or the evaporator is advantageously recirculated to the hydrolysis stage in process step (a) and the excess is taken off from the process. The column or evaporator is designed in a manner known and customary to those skilled in the art.

The stream which is produced by concentration and comprises formic acid, water and formate can be combined with the corresponding formate forming a mixture comprising the acid formate and water in step (ii), for example, between the column and the crystallization apparatus, for example by combining two lines, or they can be combined in a separate mixing apparatus, or in the crystallization apparatus itself. The corresponding formate in this case is preferably used as aqueous solution.

The crystallization procedure is generally known to those skilled in the art, with the precise design and procedure being able to be performed in the customary manner. Generally, the crystallization is carried out at a temperature in the range from −20° C. to +80° C., and preferably from 0° C. to 60° C. Generally, the amount of product crystallized out increases with decreasing temperature. The crystallization can in principle be carried out in all apparatuses known for this purpose. Said embodiment is particularly advantageously usable for removing acid formates which can crystallize in the desired composition. Relevant examples are potassium diformate (HCOOK.HCOOH), sodium diformate (HCOONa.HCOOH), sodium tetraformate (HCOONa.3HCOOH) or mixtures thereof. The formates or acid formates which have crystallized out are generally removed by customary and known methods, for example by filtration or centrifugation.

The mother liquor which is produced in the crystallization of the solid acid formate is recirculated in step (iv) to step (i). Since this mother liquor still comprises a considerable proportion of product of value, isolation thereof is thus also ensured. However, alternatively, it is also possible to use the product of value present in the motehr liquor in another manner, for example by direct use as solution.

Likewise, preference is given to a variant in which, in process stage (c)
(i) the stream from the process stage (b) comprising the formic acid and the water is combined with the corresponding formate to form a mixture comprising the acid formate and water in a column or an evaporator with removal of water by distillation; and
(ii) solid acid formate is separated off by spray granulation, spray-drying or melt crystallization from the mixture obtained from step (i) comprising acid formate and water, and this solid acid formate is isolated.

The two streams can be combined in step (i) upstream of the column or the evaporator, for example by joining two lines, or they can be combined in a seprate mixing apparatus or in the column or in the evaporator, for example via two separate feeds. The corresponding formate is preferably used as aqueous solution here.

The column or the evaporator in step (i) is generally to be operated in such a manner that a portion of the water fed can be taken off, for example overhead. The remaining acid-formate-containing mixture, which generally has a water content of from 0.5 to 30% by weight, is withdrawn as bottoms product. In particular in the isolation of the acid formate by means of melt crystallization, a lower water content of generally ≦1% by weight is set in the bottoms product. Said procedure has the advantage of a certain concentration of the stream comprising the acid formate. The water withdrawn from the column or the evaporator is advantageously recirculated to the hydrolysis stage in process step (a) and the excess is taken off from the process. The column or the evaporator is designed in the manner known and customary to those skilled in the art.

The spray granulation, spray-drying and melt crystallization procedures are generally known to those skilled in the art, in which case the precise design and procedure can be carried out in the customary manner. The abovementioned methods can also particularly advantageously be used for removing acid formates which can be crystallized in the desired composition. Relevant examples are potassium diformate (HCOOK.HCOOH), sodium diformate (HCOONa.HCOOH), sodium tetraformate (HCOONa.3HCOOH) or mixtures thereof.

Since in spray granulation, spray-drying and melt crystallization, advantageously an aqueous acid formate having a low water content can be used, generally, also, only a small proportion of condensate or free formic acid is obtained.

Depending on the amount produced and the residual concentration of acid formate present, it may also be advantageous not to recirculate the stream, but to eject it from the system.

The corresponding formates which are to be fed to the process stage (c) in the inventive process can be prepared in the most varied manners. A general overview of known and technically relevant processes for preparing formates is given, for example, in Ullmann's Encyclopedia of Industrial Chemistry, $6^{th}$ edition, 2000 electronic release, Chapter "FORMIC ACID, Derivatives, Salts". Further suitable preparation processes are also described, for example, in U.S. Pat. No. 3,262,973.

The inventive process can be carried out in principle batchwise, semicontinuously or continuously. Preferably, the inventive process is carried out continuously.

Preferably, in the inventive process, the acid formate prepared is acid metal formates, particularly preferably acid potassium formate, acid sodium formate, acid calcium formate or mixtures thereof and very particularly preferably potassium diformate (HCOOK.HCOOH), sodium diformate (HCOONa.HCOOH), sodium tetraformate (HCOONa.3HCOOH) or mixtures thereof.

The acid formates are generally prepared in the form of their solutions, or crystalline as solids. If appropriate, they can further be admixed with other components, for example other formate salts. In the case of the crystalline acid formates, it is generally advantageous for storage, transport and use to compact these together with a desiccant, for example silicates or starch, to form a particulate compactate or diverse shaped bodies, for example tablets or beads.

Preferably, in the inventive process, the acid formate prepared is an acid metal formate and the metal formate to be supplied in the process stage (c) is prepared by carbonylating the corresponding metal hydroxide.

The acid metal formate generally comprises, as possible inorganic cations, the monovalent and/or polyvalent metal cations of the metals from groups 1 to 14 of the Periodic Table of the Elements, for example lithium ($Li^+$), sodium ($Na^+$), potassium ($K^+$), cesium ($Cs^+$), magnesium ($Mg^{2+}$), calcium ($Ca^{2+}$), strontium ($Sr^{2+}$) and barium ($Ba^{2+}$), and preferably sodium ($Na^+$), potassium ($K^+$), cesium ($Cs^+$) and calcium ($Ca^{2+}$).

Said carbonylation proves particularly advantageous, in particular since it makes it possible to use readily and simply accessible starting materials and is technically simple to carry out. Thus, for example, in accordance with A. F. Hollemann, N. Wiberg, Lehrbuch der anorganischen Chemie [Textbook of Inorganic Chemistry], Walter de Gruyter Verlag Berlin New York, 1985, 91st-100th edition, page 722 sodium formate may be prepared by introducing carbon monoxide into sodium hydroxide solution at from 150 to 170° C. and a pressure of from 3 to 4 bar, and in accordance with page 947 of said textbook, potassium formate may be prepared by the action of carbon monoxide on an aqueous solution of potassium sulfate and lime at 230° C. and 30 bar. According to Ullmann's Encyclopedia of Industrial Chemistry, $6^{th}$ edition, 2000 electronic release, Chapter "FORMIC ACID, Prodution, Other Processes", sodium formate can be produced, for example, by the action of carbon monoxide on aqueous sodium hydroxide solution at 180° C. and from 1.5 to 1.8 MPa, using a reaction tower. The aqueous sodium hydroxide solution trickles in this case from the top to the bottom, whereas the carbon monoxide flows in countercurrent from bottom to top.

Generally, the preferred carbonylation to give the corresponding metal formates is performed in the inventive process in the presence of a catalyst at a temperature of from 20 to 250° C., preferably from 30 to 160° C., and particularly preferably from 90 to 120° C., and at a pressure of from 0.1 to 12 MPa absolute, and preferably from 0.3 to 6 MPa absolute.

The catalyst used is at least one catalyst selected from the group consisting of the alcohols and formic esters. In principle, all catalysts are suitable in which the metal hydroxides dissolve readily. Suitable catalysts are, for example, saturated unbranched $C_1$-$C_4$ alkanols, unsaturated unbranched $C_3$-$C_4$ alkanols, saturated branched $C_3$-$C_4$ alkanols and unsaturated branched $C_4$ alkanols, and formic esters thereof. If an alcohol in a mixture with a formic ester is used as catalyst, generally the formic ester of this alcohol is used. Preference is given to use of saturated unbranched $C_1$-$C_4$ alkanols and saturated branched $C_3$-$C_4$ alkanols, particularly preferably methanol. The catalyst is generally used at a concentration of from 1 to 40% by weight, preferably from 5 to 25% by weight, particularly preferably from 10 to 20% by weight, based on the total reaction solution.

Compared with otherwise customary processes for formate preparation, operations can be carried out at higher concentration ranges of the metal hydroxide and with a trend toward higher pressures and lower temperatures. Since the reaction is limited by mass transfer, higher space-time yields can be achieved by good mixing, for example using mixing nozzles.

The reaction can be carried out either continuously or batchwise. Preference is given to a continuous reaction. Generally, the reaction is carried out in such a manner that the metal hydroxide is converted virtually quantitatively to the metal formate. The reaction is advantageously carried out until the content of metal hydroxide in the reaction solution is less than 0.1% by weight, preferably less than 0.04% by weight, particularly preferably less than 0.01% by weight.

The reaction can in principle be carried out in any type of reaction apparatus. Preferably, it is carried out in a stirred tank having a gas-introduction device, in a bubble column or in a loop reactor. Particularly preferably, the reaction is carried out in a loop reactor or a bubble column, very particularly in a loop reactor, since in this case, on account of the high interface area between the metal hydroxide and catalyst-containing water-containing solution and the carbon monoxide introduced, a high absorption rate results, and thus also a high reaction rate. When a bubble column is used, the carbon monoxide can be fed, for example, in the upper region (cocurrent procedure) or else in the lower region (countercurrent procedure).

The metal hydroxides are generally used as aqueous solution. The concentration of these metal hydroxide solutions is generally from 25 to 50% by weight, preferably from 45 to 50% by weight, particularly preferably 48.5 to 50% by weight. The aqueous soltuion can also comprise a plurality of metal hydroxides. Generally, no special requirements are made of the purity of the metal hydroxide solutions used. Therefore, generally, technical grade metal hydroxide solutions can be used. The preferred inventive process may also be carried out using pure metal hydroxide solutions. Preference is given to the hydroxides of sodium, potassium and/or calcium.

Carbon monoxide can be used not only as individual component, but also in a mixture with other gases, for example nitrogen or noble gases. If carbon monoxide is used in a mixture with other gases, the content of carbon monoxide in the gas mixture should be at least 5% by volume, preferably at least 10% by volume, particularly preferably at least 25% by volume, and very particularly preferably at least 50% by volume. The carbon monoxide partial pressure during the reaction should generally be from 0.1 to 12 MPa, and preferably from 2 to 6 MPa. Generally, no special requirements are made of the purity of the carbon monoxide or corresponding carbon-monoxide-containing gas mixture used. The reaction may therefore be carried out not only with pure carbon monoxide, but also with technical grade carbon monoxide or carbon-monoxide-containing gas mixtures.

Said reaction procedure ensures that crystallization or precipitation of metal formate does not occur, since the reaction mixture is present as solution for the period of the reaction and precipitation of solids and blockage of piping are avoided.

The metal formates obtained by the carbonylation described are generally present in the reaction solution at a concentration of from 10 to 90% by weight, preferably from 30 to 80% by weight, and particularly preferably from 40 to 70% by weight.

Particularly preferably (i), in the inventive process, the carbonylation is carried out in the presence of methanol as catalyst, (ii) the resultant reaction mixture comprising metal formate, water and methanol, together with the stream from the process stage (b) comprising methanol with or without methyl formate are separated by distillation into a methanol-containing stream, if appropriate into a stream comprising methyl formate, and a stream comprising the metal formate and water, and (iii) the resultant stream comprising the metal formate and water is fed to process stage (c).

Preferably, step (ii) is carried out in a column by feeding as feed the stream from the process stage (b) comprising methanol with or without methyl formate and feeding, beneath the abovementioned feed, the reaction mixture comprising the metal formate, water and methanol resulting from the carbonylation. The low-boiling components methyl formate and methanol ascend, whereas the metal formate and water descend and are withdrwan as bottoms product. The lowest-boiling component is withdrawn as overhead product. If, from the process stage (b) a stream comprising methanol and also methyl formate is fed, as is particularly preferred, a stream comprising methyl formate is withdrawn as overhead product from the column. This stream is preferably recirculated to the process stage (a) for hydrolysis. The methanol-containing stream is produced in this case as a side stream in the upper region of the column. Since methyl formate is generally prepared by carbonylating methanol, it is particularly advantageous to recirculate the methanol-containing stream as starting material for the preparation of methyl formate, in which case the methanol to be recirculated in this varient can certainly also comprise residual amounts of methyl formate. Thus, in the overall balance, it is only necessary to replace the small methanol losses by fresh methanol.

It must be emphasized that in the described separation and recirculation of the methanol-containing stream for the preparation of methyl formate, further steps can be provided as intermediates. Thus, if appropriate, it is advantageous, in step (ii) to produce a methanol stream still comprising methyl formate and to separate this, in a downstream column, from the residual methyl formate, with this generally also being recirculated for hydrolysis to the process stage (a). The methanol-containing bottoms product of this downstream column is then generally fed to the methyl formate preparation, in which case the amount of methanol required to catalyze the carbonylation can be fed to the carbonylation reactor.

In a particularly preferred embodiment, the simplified process flow chart which is shown in FIG. 1, via line (1), methyl formate and water comprising formic acid which is recirculated from the process are added to the cascade hydrolysis reactor (A). Generally, the two starting materials are brought to the desired inlet temperature in a heat exchanger premixed (as shown in the flow chart) or separately. The reaction mixture originating from the hydrolysis stage (process stage (a)), which reaction mixture comprises unreacted methyl formate, water, formic acid and methanol, is fed via line (2) to the column (B) in which the reaction mixture is separated by distillation into an overhead stream comprising methyl formate and methanol, and a bottoms stream comprising aqueous formic acid (process stage (b)). The overhead stream comprising methyl formate and methanol is fed via line (3) to column (C). In addition, the reaction mixture comprising metal formate, water and methanol from the carbonylation is fed to the column (C) beneath the inlet point of the stream comprising methyl formate and methanol via line (12). Methyl formate is obtained overhead from column (C) via line (4) and is recirculated to the process stage (a) for the hydrolysis. A methyl-formate-containing methanol stream is obtained via a sidestream takeoff in the upper region of the column and is fed via line (6) to the column (D). In this column the stream is separated into a methyl formate overhead stream which is recirculated via line (7) to the process stage (a) for the hydrolysis also, and a methanol bottoms stream, which is recirculated via line (5) for the preparation of methyl formate, with the amount of methanol required to catalyze the carbonylation being fed to the carbonylation reactor. The carbonylation for preparing the corresponding formate is performed in reactor (H). To this is fed aqueous metal hydroxide, particularly preferably potassium hydroxide solution, via line (8), and carbon monoxide is fed via line (9). Line (10) serves primarily for retaining pressure and if appropriate for ejecting the purge stream. At the bottom end of column (C), a portion of the water is withdrawn and recirculated via line (11) to the hydrolysis stage. The bottoms product obtained is an aqueous metal formate solution. The stream comprising aqueous formic acid from process stage (b) is fed via line (14) to the column (E). If appropriate, a portion of the aqueous metal formate solution from column (C) is also fed via lines (13) and (13*b*). The column (E) is advantageously operated in such a manner that the bottoms product obtained is a concentrated mixture comprising formic acid, metal formate and water having a water content of generally from 10 to 40% by weight. A portion of the water is withdrawn from the column (E) in the form of a formic-acid-containing water stream as overhead product and recirculated via line (19) to the hydrolysis stage. A portion of the water stream comprising small amounts of formic acid can here optionally be withdrawn from the system via line (18). The bottoms product of column (E) is fed via line (15) to an apparatus (G) suitable for crystallization, for example a cooling disc crystallizer. The aqueous metal formate solution from column (C) is fed via line (13*a*). The feed in this case can be performed, for example, in the lower region of column (E), by combining two lines (as shown in FIG. 1) or directly into the crystallization apparatus. The crystallization is primarily performed by temperature decrease. The resultant crystals are fed together with the supernatant solution for separation to the apparatus (F). Preferably the separation is performed by centrifugation. The separated crystals are withdrawn via line (16) and can be dried and/or compounded, for example in optional following stages. The resultant mother liquor is recirculated via line (17) to the column (E).

Figure 2:
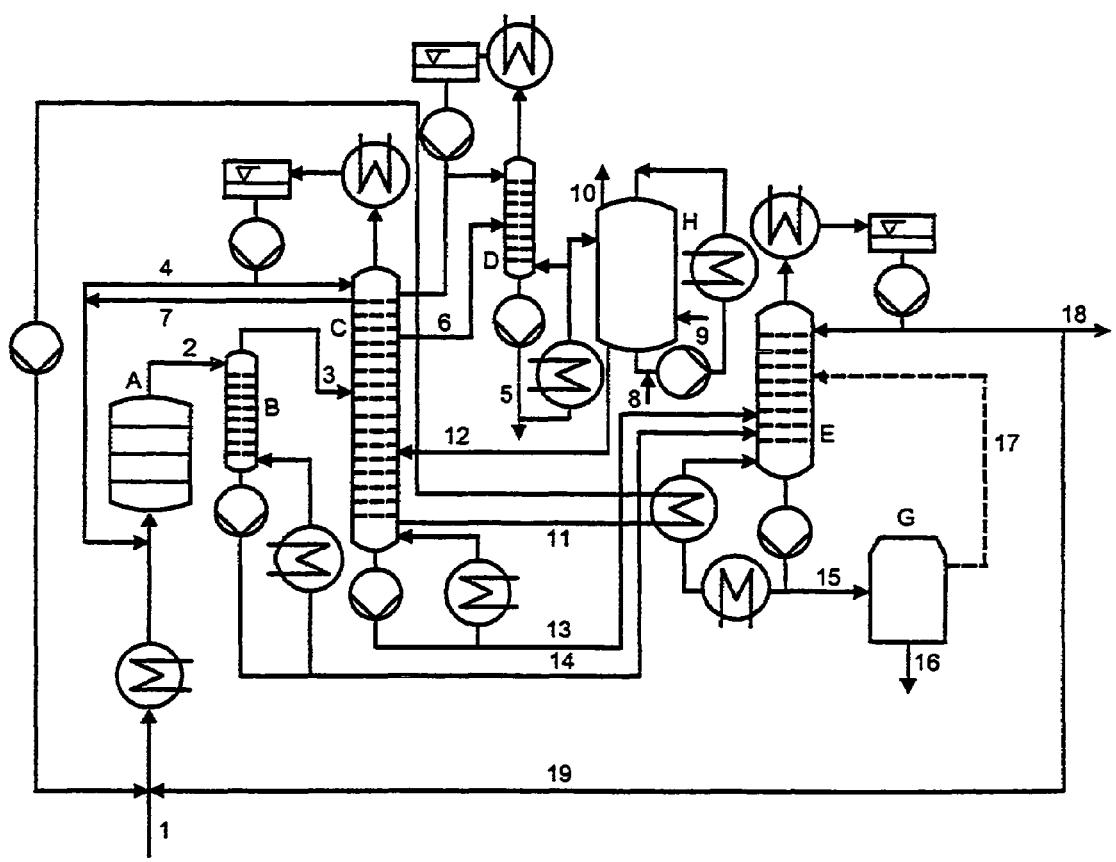

In another particularly preferred embodiment, whose simplified process flow chart is shown in FIG. 2, the process stages (a) and (b) and the preparation of the metal formate, preferably of the potassium formate, and the operation of the columns (C) and (D) are carried out as described in the above particularly preferred embodiment. The stream comprising the aqueous formic acid from the process stage (b) is fed via line (14) and the stream comprising the aqueous metal formate solution from column (C) is fed via line (13) to the column (E). The column (E) is advantageously operated in such a manner that the bottoms product obtained is a concentrated mixture comprising formic acid, metal formate and water having a water content generally from 0.5 to 30% by weight. A portion of the water fed is withdrawn from the column (E) as overhead product in the form of a formic-acid-containing water stream and is recirculated via line (19) to the hydrolysis stage. A portion of the water stream comprising small amounts of formic acid can here optionally be withdrawn from the system via line (18). The bottoms product of the column (E) is fed via line (15) to an apparatus (G) suitable for spray granulation, spray drying or melt crystallization. The resultant solid acid formate is withdrawn via line (16) and can be dried and/or compounded, for example in optional following stages. The resultant condensate can optionally be recirculated via line (17) to the column (E) or ejected from the system.

The inventive process makes it possible to prepare acid formates on an industrial scale in high yield and high space-time yield, with simultaneously high flexibility with respect to composition and using readily accessible raw materials with simple process design and low capital costs. In addition, the process has the critical advantage that the required formic acid can be produced directly from the methyl formate without the costly diversion, which is expensive in terms of resources, via the concentrated formic acid, whereas the required formate can be obtained for example in a simple manner by carbonylation using easily accessible starting materials. The inventive process is therefore simple to carry out in processing terms and compared with the processes involving direct use of concentrated formic acid according to the prior art, has markedly lower capital costs and a markedly lower energy consumption. In addition, in part the use of high-alloy steels can be avoided, since the acid formates are much less corrosive than concentrated formic acid.

In addition, the invention relates to an apparatus for preparing the acid formates according to the inventive process, comprising (a) a reactor (A) suitable for hydrolyzing methyl formate;

(b) a column (B) suitable for separating by distillation a stream comprising methyl formate, formic acid, methanol and water into methyl formate, methanol and a stream comprising formic acid and water, which column is connected on the feed side to the reactor (A);

(c) a column (E) suitable for removing water from a stream comprising formic acid and water, which column is connected on the feed side to the column bottom of column (B).

A suitable reactor (A) is, for example, a stirred tank or a jet loop reactor. Preference is given to a cascade reactor. The reactor (A) is designed according to the manner customary and known to those skilled in the art.

The columns (B) and (E) are designed in the manner which is customary and known to those skilled in the art.

A preferred apparatus is an apparatus which, in addition to the abovementioned features (a) to (c), comprises (d) an apparatus (G) suitable for crystallizing acid formate, which apparatus is connected on the feed side to the column bottom of column (E) and to a possible supply of aqueous formate;

(f) an apparatus (F) suitable for separating off crystals of the acid formate, which apparatus is connected on the feed side to apparatus (G); and (g) a connection line (17) between apparatus (F) and column (E), which connection line is suitable for recirculating mother liquor.

The apparatuses (G) and (F) are designed in the manner which is customary and known to those skilled in the art.

Furthermore, the preferred apparatus is an apparatus which, in addition to the abovementioned features (a) to (c), comprises (e) a possible supply to the column (E), which possible supply is suitable for feeding aqueous formate; and (f) an apparatus (G) suitable for spray granulation, spray drying or melt crystallization, which apparatus is connected on the feed side to the column bottom of column (E).

The apparatus (G) is designed in the manner which is customary and known to those skilled in the art.

In addition, the invention relates to the use of the inventively prepared acid formates for preserving and/or acidifying plant and animal materials. Examples are the use of acid formates for preserving and acidifying grass, agricultural plants, fish and fish products and meat products, as are described, for example, in WO 97/05783, WO 99/12435, WO 00/08929 and WO 01/19207.

Furthermore, the invention relates to the use of the inventively prepared acid formates for treating biowastes. The use of acid formates for treating biowastes is described, for example, in WO 98/20911.

In addition, the invention relates to the use of the inventively prepared acid formates as additive in animal nutrition and/or as growth promoters for animals, for example for breeding sows, growing/finishing pigs, poultry, calves, cows and fish. Said use is described, for example, in WO 96/35337. Preference is given to the use of the inventively prepared acid potassium formates, in particular potassium diformate, as additive in animal nutrition and/or as growth promoters for animals, in particular for breeding sows and growing/finishing pigs.

Very particularly preferred mixtures for the preferred use of the acid potassium formates prepared by the inventive process as additive in animal nutrition and/or as growth promoters for animals are the following two compositions:

|  | Mixture 1 (% by weight) | Mixture 2 (% by weight) |
| --- | --- | --- |
| Potassium diformate | 20 to 60 | 60 to 99 |
| Sodium diformate/tetraformate | 20 to 50 | — |
| Calcium formate | 0 to 25 | 0 to 28 |

| | Mixture 1 (% by weight) | Mixture 2 (% by weight) |
|---|---|---|
| Dessicant (silicate or starch) | 0 to 4 | 0 to 4 |
| Water | 0 to 5 | 0 to 5 |

Very particular preference is given to the use of the inventively prepared potassium diformate as additive in animal nutrition and/or as growth promoter for animals in the form of a product of composition 98.0±1% by weight potassium diformate, 1.5±1% by weight silicate and 0.5±0.3% by weight water.

We claim:

1. A process for preparing acid formates comprising:
   (a) partially hydrolyzing methyl formates with water;
   (b) separating off by distillation methyl formate and methanol from the reaction mixture obtained in process stage (a), forming a stream comprising formic acid and water; and
   (c) combining the stream comprising formic acid and water from the process stage (b) with the corresponding formate forming a mixture comprising the acid formate and water.

2. A process according to claim 1, wherein, in the process stage (a), the methyl formate and the water are fed in a molar ratio of 0.1 to 1.

3. A process according to claim 1, wherein the methyl formate separated off in process stage (b) is recirculated to process stage (a).

4. A process according to claim 1, wherein, in the process stage (d):
   (i) the stream comprising the formic acid and the water from the process stage (b), together with the mother liquor recirculated from step (iv), is concentrated in a column or an evaporator with removal of water by distillation;
   (ii) the stream which was produced from step (i) by concentration and comprises formic acid, water and formate is combined with the corresponding formate, forming a mixture comprising the acid formate and water;
   (iii) solid acid formate from the mixture comprising acid formate and water obtained from step (ii) is precipitated by crystallization and this is isolated; and
   (iv) the resultant mother liquor is recirculated to step (i).

5. A process according to claim 1, wherein, in process stage (c):
   (i) the stream from the process stage (b) comprising the formic acid and the water and the corresponding formate are combined to form a mixture comprising the acid formate and water in a column or an evaporator with removal of water by distillation; and
   (ii) solid acid formate is separated off by spray granulation, spray drying or melt crystallization from the mixture obtained from step (i) comprising acid formate and water, and this solid acid formate is isolated.

6. A process according to claim 1, wherein the acid formate prepared is an acid metal formate and the metal formate to be supplied in process stage (c) is produced by carbonylating the corresponding metal hydroxide.

7. A process according to claim 6, wherein:
   (i) the carbonylation is carried out in the presence of methanol as catalyst;
   (ii) the resultant reaction mixture comprising metal formate, water and methanol together with the stream comprising methanol with or without methyl formate from the process stage (b) is separated by distillation into a stream comprising methanol, with or without a stream comprising methyl formate and a stream comprising the metal formate and water; and
   (iii) the resultant stream comprising the metal formate and water is fed to the process stage (c).

8. A process according to claim 1, wherein the acid formate prepared is selected from the group consisting of acid potassium formate, acid sodium formate, acid calcium formate and mixtures thereof.

9. A process according to claim 1, wherein the acid formate prepared is selected from the group consisting of potassium diformate, sodium diformate, sodium tetraformate and mixtures thereof.

10. A process according to claim 2, wherein the methyl formate separated off in process stage (b) is recirculated to process stage (a).

11. A process according to claim 2, wherein, in the process stage (d):
    (i) the stream comprising the formic acid and the water from the process stage (b), together with the mother liquor recirculated from step (iv), is concentrated in a column or an evaporator with removal of water by distillation;
    (ii) the stream which was produced from step (i) by concentration and comprises formic acid, water and formate is combined with the corresponding formate, forming a mixture comprising the acid formate and water;
    (iii) solid acid formate from the mixture comprising acid formate and water obtained from step (ii) is precipitated by crystallization and this is isolated; and
    (iv) the resultant mother liquor is recirculated to step (i).

12. A process according to claim 3, wherein, in the process stage (d):
    (i) the stream comprising the formic acid and the water from the process stage (b), together with the mother liquor recirculated from step (iv), is concentrated in a column or an evaporator with removal of water by distillation;
    (ii) the stream which was produced from step (i) by concentration and comprises formic acid, water and formate is combined with the corresponding formate, forming a mixture comprising the acid formate and water;
    (iii) solid acid formate from the mixture comprising acid formate and water obtained from step (ii) is precipitated by crystallization and this is isolated; and
    (iv) the resultant mother liquor is recirculated to step (i).

13. A process according to claim 2, wherein, in process stage (c):
    (i) the stream from the process stage (b) comprising the formic acid and the water and the corresponding formate are combined to form a mixture comprising the acid formate and water in a column or an evaporator with removal of water by distillation; and
    (ii) solid acid formate is separated off by spray granulation, spray drying or melt crystallization from the mixture obtained from step (i) comprising acid formate and water, and this solid acid formate is isolated.

14. A process according to claim 3, wherein, in process stage (c):
    (i) the stream from the process stage (b) comprising the formic acid and the water and the corresponding formate are combined to form a mixture comprising the acid formate and water in a column or an evaporator with removal of water by distillation; and (ii) solid acid formate is separated off by spray granulation, spray drying or melt crystallization from the mixture obtained from step (i) comprising acid formate and water, and this solid acid formate is isolated.

15. A process according to claim 2, wherein the acid formate prepared is an acid metal formate and the metal formate to be supplied in process stage (c) is produced by carbonylating the corresponding metal hydroxide.

16. A process according to claim 3, wherein the acid formate prepared is an acid metal formate and the metal formate to be supplied in process stage (c) is produced by carbonylating the corresponding metal hydroxide.

17. A process according to claim 4, wherein the acid formate prepared is an acid metal formate and the metal formate to be supplied in process stage (c) is produced by carbonylating the corresponding metal hydroxide.

18. A process according to claim 5, wherein the acid formate prepared is an acid metal formate and the metal formate to be supplied in process stage (c) is produced by carbonylating the corresponding metal hydroxide.

* * * * *